United States Patent [19]

Duffy

[11] Patent Number: 4,841,983
[45] Date of Patent: Jun. 27, 1989

[54] SPATIAL TRAJECTORY ANALYSIS IN BRAIN ELECTRICAL ACTIVITY MAPPING

[76] Inventor: Frank H. Duffy, 1990 Commonwealth Ave., Brighton, Mass. 02135

[21] Appl. No.: 38,037

[22] Filed: Apr. 13, 1987

[51] Int. Cl.$^4$ .............................................. A61B 5/04
[52] U.S. Cl. ................................................... 128/731
[58] Field of Search ............................... 128/731–732; 364/415–417

[56] References Cited

U.S. PATENT DOCUMENTS 4,421,122  12/1983  Duffy .................................. 128/731

OTHER PUBLICATIONS

Duffy et al., "Brain Electrical Activity Mapping (BEAM): A Method for Extending the Clinical Utility of EEG and Evoked Potential Data", Ann. Neurol., 5:309-321 (1979).
Duffy et al., "Significance Probability Mapping: An Aid in the Topographic Analysis of Brain Electrical Activity", Electroencephalography and Clinical Neurophysiology, 51:455-462 (1981).
Duffy et al., "Topographical Display of Evoked Potentials: Clinical Applications of Brain Electrical Activity Mapping (BEAM)", Anals New York Academy of Sciences, 388:183-196 (1982).
Duffy et al., "Tumor Detection from Topographic Maps of Long Latency Evoked Potentials: Spatial Trajectory Analysis and Cross Correlational Analyses", unpublished paper.
Sandini et al., "Topography of Brain Electrical Activity: A Bioengineering Approach," Med. Prog. Through Technology 10:5-19 (1983).

*Primary Examiner*—Francis Jaworski

[57] ABSTRACT

A method is disclosed for utilizing brain evoked potentials for characterizing brain pathology. A brain electrical activity map is prepared from a patient's evoked potential data, and the centers of gravity of peaks of the evoked potential are calculated for a sequence of frames of the map, and plotted in a single frame to provide a spatial trajectory which may then be compared to a patient norm in order to detect and characterize brain pathology.

14 Claims, 7 Drawing Sheets

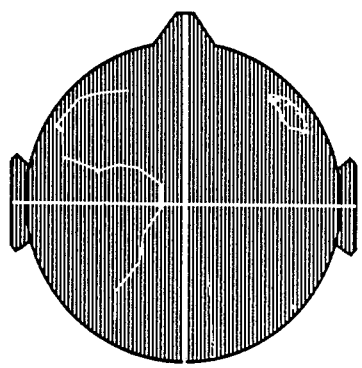
FIG 10 (AMPL)
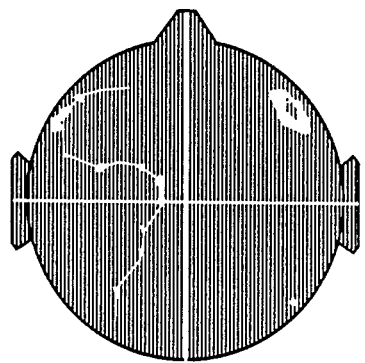
FIG 11 (VEL$^{-1}$)
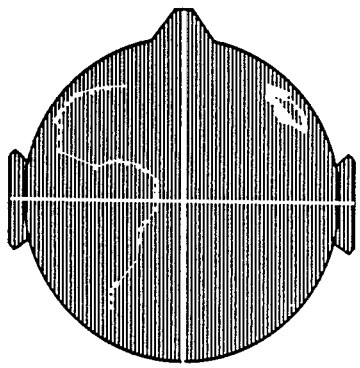
FIG 12 (AMP/VEL)
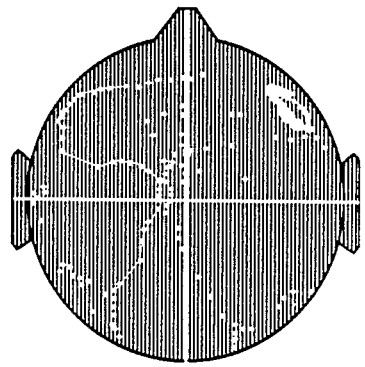
FIG 13 (AMP/VEL)

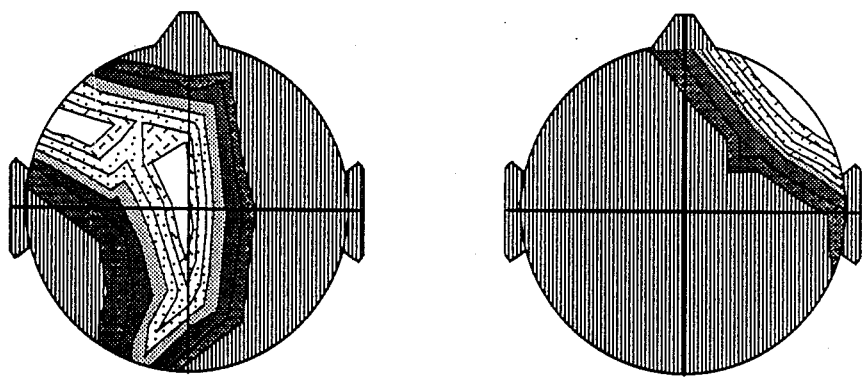
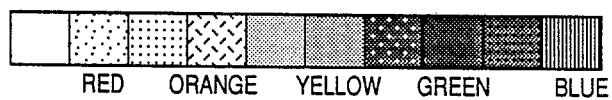
FIG 14

SPATIAL TRAJECTORY ANALYSIS IN BRAIN ELECTRICAL ACTIVITY MAPPING

BACKGROUND OF THE INVENTION

This invention relates to the measurement of brain electrical activity.

Such measurement is based on the localized discrete sampling, both in space and time, of a biological variable. In multichannel evoked potentials (EPs) the underlying biological event is both space and time-variant. To analyze the scalp-recorded activity generated by such events, spatiotemporal relationships must be explicit. This is readily apparent by inspecting the dynamic evolution of topographic maps generated by even simple sensory stimulations. Although topographic maps make biological events more comprehensible, they do not simplify the quantitative evaluation of the phenomenon; on the contrary, new and more complex features are made evident. Expressions such as slowing, lateralized, persistent, focal, and asymmetrical are often used to describe these complex phenomena. Such subjective terminology may be descriptive of the findings but is not easily amenable to a quantitative evaluation. There is a a need to quantify these subjective judgments. Doing so will enhance the diagnostic power of event-related potentials.

It is known in the art to use topographic mapping to aid in the clinical evaluation of evoked potential (EP) data. In general, single topographic images of evoked potential (EP) data are formed every 4 msec and then all 128 images are displayed in rapid, recurring sequence. Thus, the spatial distribution or positive (red) and negative (blue) activities can be viewed by this "cartooning" process over the entire 512 msec EP epoch. Normal subjects characteristically demonstrate symmetrical negative or positive foci that appear and disappear as a function of time, often moving in an anterior or posterior direction. Concurrent positive and negative foci may coexist. In the face of pathology, this pattern becomes distorted. Regions of abnormality may show either diminished or greatly augmented activities or both at different times. Topographic movies in pathology often demonstrate asymmetrical foci. Positive or negative potential "hills" may sweep along the medial-lateral axis rather than along the more usual A-P axis. Clinical experience has shown such movies to be of considerable value in the identification of pathology. Subtle shifts of the spatial distribution of a potential hill or in the trajectory of its sweep across the head may serve to define the location of a lesion.

It is known to compute the trajectory of an evoked potential of normal subjects to visual stimuli by plotting the center of gravities of the sequence of topographic maps representing the evoked potential. Sandini et al., "Topography of Brain Electrical Activity: A Bioengineering Approach," *Med Prog. through Technology* 10: 5-19 (1983).

Brain electrical activity mapping (BEAM) is a known diagnostic tool for detecting brain abnormalities. BEAM is described in U.S. Pat. No. 4,421,122; Duffy et al., "Brain Electrical Activity Mapping (BEAM): A New Method for Extending the Clinical Utility of EEG and Evoked Potential Data," Ann. Neurol., 5: 309-321 (1979); Duffy, Bartels, et al., Significance Probability Mapping: An Aid to the Topographic Analysis of Brain Electrical Activity," Electroenceph. Clin. Neurophysiol., 512: 455-462 (1981); Duffy, *Topographic Mapping of Brain Electrical Activity*, Butterworths (1986) (all incorporated by reference).

SUMMARY OF THE INVENTION

In general the invention features an improved technique for recognizing and characterizing brain pathology by plotting the trajectory of an evoked potential. In preferred embodiments: a plurality of trajectories (e.g., negative and positive) are plotted; the centers of gravity of the peak regions of each frame form the points of the trajectory; the peak regions are defined as those areas exceeding a preselected percentage of the maximum value of the frame; points are not included in the trajectory if the maximum value in the frame does not exceed a noise floor, a percentage of the maximum value of all frames (e.g., 10 to 25%); the balance point of the trajectory is provided as a further diagnostic tool; an expression consisting of the amplitude of the peak divided by the velocity of movement of the peak (AMP/VEL) is computed and displayed; and unusually high values of a numerical feature such as AMP/VEL are displayed along the spatial trajectory as enlarged points.

The new spatial trajectory analysis (STA) provies an improved diagnostic tool for detecting and characterizing brain pathology. An advantage of the technique is that the patient's evoked potential cartoon (which previously would have to viewed on a computer monitor by each physician performing a diagnosis) is reduced to a single image, which can be easily reproduced and transmitted.

Other features and advantages of the invention will be apparent from the following description of preferred embodiments and from the claims.

DESCRIPTION OF THE PREFERRED EMBODIMENT

Drawings

FIGS. 10-13 are spatial trajectory plots for a subject with a right lateral frontal tumor.

FIG. 14 shows plots of the distribution of negative and positive center of gravity (COG) for the STA shown in FIGS. 10-13.

Method

Figure 1:
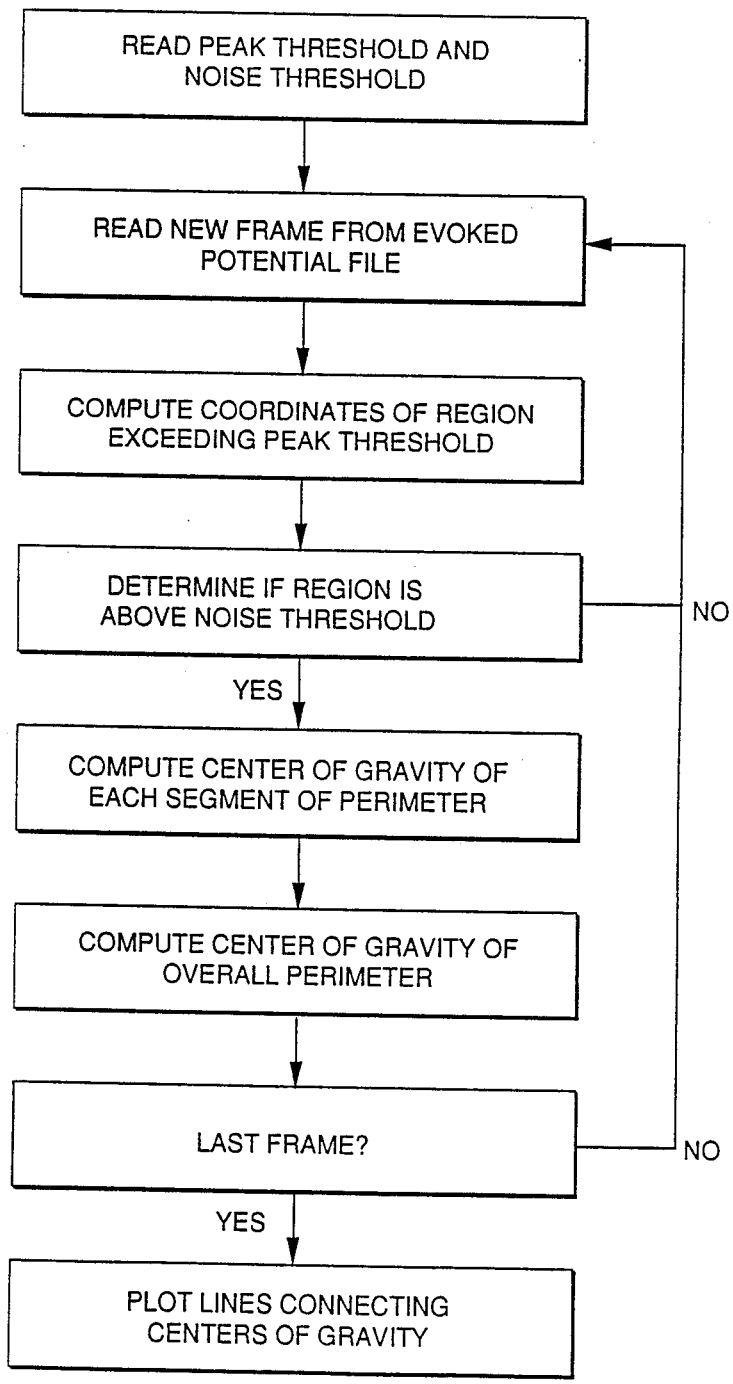
FIG. 1 is an overall block diagram of the method of preparing a plot representing the spatial trajectories of an evoked potential.
Figure 2:
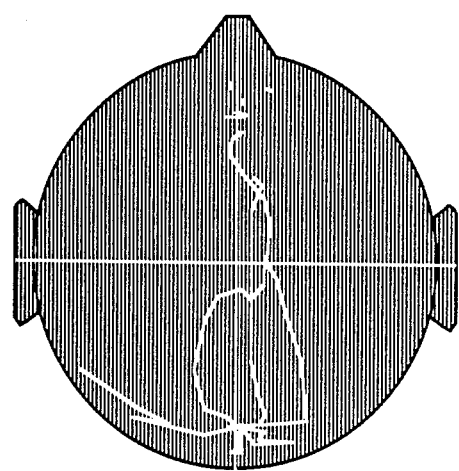
FIGS. 2-5 are spatial trajectory plots for normal subjects.
Figure 3:
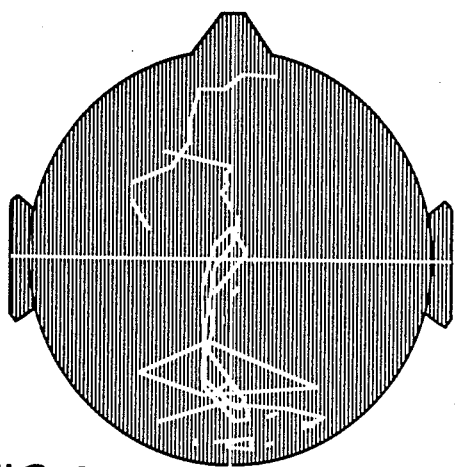
Figure 4:
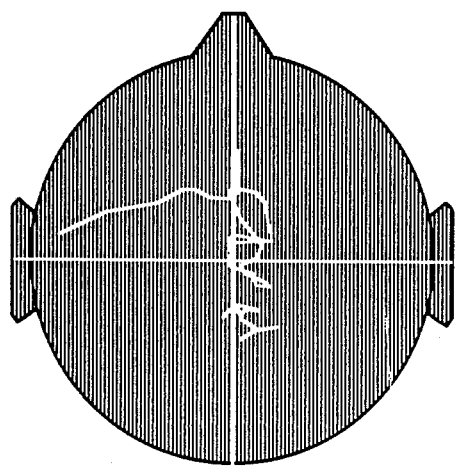
Figure 5:
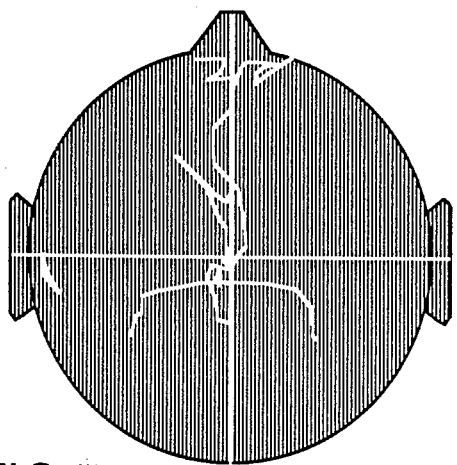

Spatial trajectory analysis, or STA, refers to a method developed to numerically capture and quantify spatial-temporal characteristics of EP data. Operationally, the trajectory of an EP can be represented by the movement of the "center of gravity" (COG) of activity calculated for each 4 msec frame. The STA algorithm computes the COG of a region whose EP amplitude exceeds a given "peak" threshold. The peak threshold is pre-set as a percent and is computed adaptively by the program as the numerical amplitude corresponding to given percentage of the maximum amplitude of each 4 msec image. In this way, it is possible to detect the position of the COG "normalized" to the energy of each 4 msec epoch.

To avoid the COG computation in frames with maxima within a "noise" range, a second "noise" threshold is defined by the user as a percentage of the maximum value for all 4 msec epochs. If a maximum in a frame is below the noise threshold, then the COG for that maximum is not computed. This avoids plotting trajectories of meaningless noise. Thus, the spatial trajectory of an evoked potential will first appear when the peak of the EP rises above the noise threshold, and the trajectory will end after the peak has decayed back to a level below the threshold. The spurious and distracting trajectories above and below the noise level are not displayed.

For each frame, then, the perimeter of the region above the threshold is determined and the COG calculated for that region making the presumption that the region has one value, the mean of all pixels within the area. This results in a much more rapid calculation than weighing each pixel separately and this simplification induces little error so long as the threshold is set reasonably high, e.g., the top 25%. The actual calculation is performed by computing the center of gravity of each segment of the perimeter, and then computing the overall center of gravity of the segments. The center of gravities are computed directly from the monodimensional data, and not from the interpolated maps, because the results are mathematically the same (owing to the nature of the linear interpolation algorithm used in producing the BEAM maps) and the computation is much faster.

An appendix to this application contains listings of the source code for several preferred versions of the software used in computing the spatial trajectories. The software operates on a Digital Equipment PDP 11/60. Copyright in the software is owned by Childrens Medical Center Corporation.

The software is capable of producing a number of descriptors, or features, for each frame, including the x and y coordinate of a plurality of COGs, the maximum amplitude above threshold, the area above threshold and maximum and minimum x and y of the area above threshold. The change in x and y (delta x and delta y) from the preceding frame are also calculated. Further, the entire EP is broken down into 26 overlapping latency epochs chosen to represent clinically coherent regions on an a priori, empirical basis. For each latency epoch the minimum, maximum, and mean value of each parameter across all images within the epoch are calculated. Thereby, numerical features, both independent and dependent of space and time, are produced. The COG algorithm also has the ability to analyze two independent trajectories per frame, one negative and one positive. This results, in most circumstances, in a separate set of features for positive and negative trajectories.

The following table summarizes features that we have found useful (those with an asterisk have been found to be the most discriminating):

LEFT VS RIGHT SIDED TUMOR STUDY

*AET1 (AER,STA) The x position of the COG, mean value in the interval 400-440 msec.

AET2 (AER,STA) Minimum of the maximum amplitude per frame in the 400-440 msec interval.

BST2 (BSE,STA) Minimum are above threshold in the 200-240 msec interval.

*BST3 (BSE,STA) Maximum x value of the boundary of the area above threshold in the 440-480 msec interval.

ANTERIOR VS CENTRAL-LATERAL VS POSTERIOR TUMOR STUDY

TAE1 (AER,STA) Minimum of the maximum amplitude per frame for the 240-280 msec interval.

TAE2 (AER,STA) Minimum of the maximum amplitude per frame for the 440-480 msec interval.

*TAE3 (AER,STA) Maximum x value of the gboundary of the area above threshold in the 200-240 msec interval.

*TAE4 (AER,STA) Mean change of the x position of the COG of the 200-240 msec interval.

*TBS1 (BSE,STA) Maximum y value of the boundary of the area above threshold in the 272-368 msec interval.

*TBS2 (BSE,STA) Mean change of y position of the COG in the 200-240 msec interval.

Clinical Results

In examining the application of spatial trajectory analysis (STA) to clinical situations, we have found the main difference between patients and normal control subjects is that the spatial evolution of the trajectory is much more complex in the clinical population. Quite often more than one region of both positive and negative polarity is present. Some of these regions eventually merge or split during their evolution. From a computational point of view, we were forced to allow for the determination of multiple CoG in a single frame.

A further observation was made that in normal subjects the topographic distribution (positive and negative maxima-peaks and troughs) of EP data changes over time in a non-random manner often showing midline anterior-posterior or symmetrical medial-lateral movement of maxima. Such peak movement has been documented by Sandini et al., "Topography of Brain Electrical Activity: A Bioengineering Approach," *Med Prog. through Technology* 10: 5-19 (1983) who used this medial-lateral motion for functional localization using VER data. Pathology, however, greatly alters this spatiotemporal pattern and induces major distortion of peak trajectories. We commonly observe that peaks appear late overlying tumors, eventually becoming above-average in amplitude, and exhibiting prolonged duration (Duffy et al., Brain electrical activity mapping (BEAM): A Method for Extending the Clinical Utility of EEG and Evoked Potential Data, *Ann Neurol* 5: 309-332, 1979b; Duffy, FH, Topographic Display of Evoked Potentials: Clinical Applications of Brain Electrical Activity Mapping (BEAM). *Ann NY Acad. Sci.* 388: 183-196, 1982).

Some examples of normal EP trajectories are presented in FIGS. 2-5. The basic pattern of all modalities is symmetrical with occasional slowing over the central and occipital areas: flash VER (FIG. 2) is mainly central-occipital; pattern-reversal VER (FIG. 3), occipital; AER (FIG. 4), central; and SER (FIG. 5), centroparietal.

Figure 6:
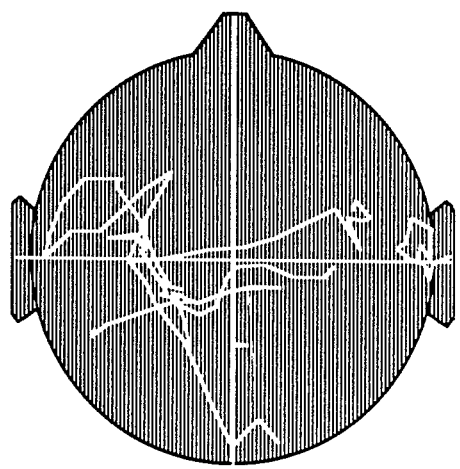
FIGS. 6-9 are spatial trajectory plots for abnormal subjects.
Figure 7:
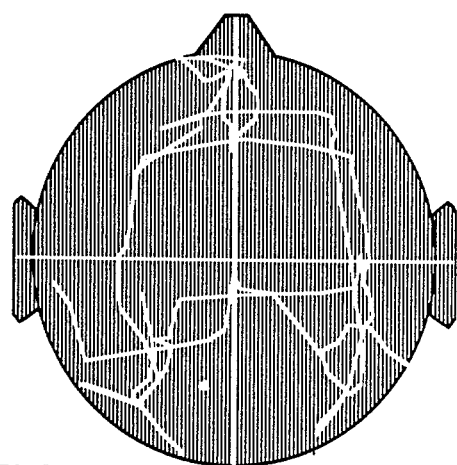
Figure 8:
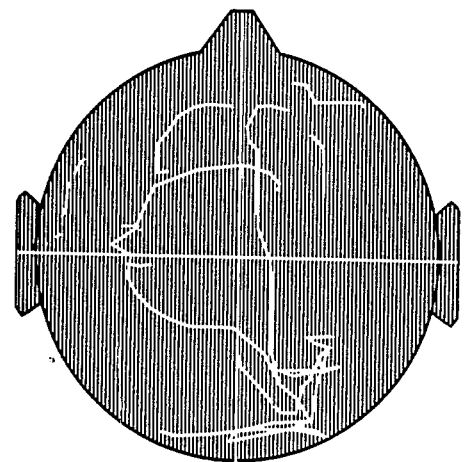
Figure 9:
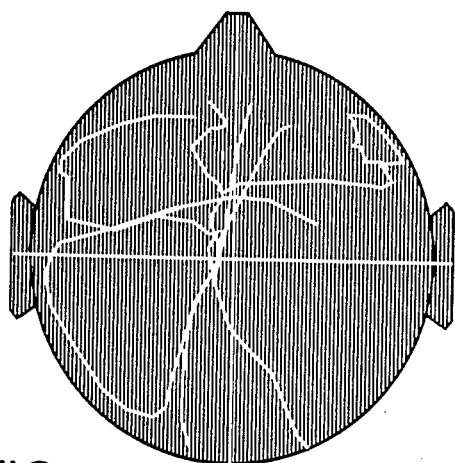

For abnormal EP, the basic pattern is a long-lasting asymmetry, often over the position of a tumor. Some examples of abnormal trajectories are presented in FIGS. 6-9: FIG. 6 shows an AER for a patient with a left posterior quadrant tumor. FIG. 7 shows a BSE for a patient with a right posterior quadrant tumor. FIG. 8 shows a pattern-reversal VER for a patient with a right posterior quadrant tumor. FIG. 9 shows an AER for a patient with a right anterior quadrant tumor.

In addition to the evident asymmetries, the focality measure (i.e., amplitude divided by velocity) sometimes proved particularly useful in determining latency and location of abnormal focal activity. For example, in FIG. 9, the maximum of the focality measure exactly pinpoints the location of the tumor.

By using features derived from the STA we have been able to classify correctly 20 of our 21 tumor cases according to the location of the tumor (i.e., right or left, anterior, central, or posterior).

Spatial trajectory analysis also produces another class of features. Pathology, such as supratentorial brain tumor, is seen to induce characteristic change in the sweep of maxima across the scalp. As previously mentioned, these EPs may deviate from the midline, from anterior-posterior movement, and may appear quite asymmetrical. Such trajectories are adequately captured by the previously described analytic features. However it is also observed that the traverse of activity overlying a tumor is often slowed and EP activity persists for a more extended time overlying such pathology. Moreover, amplitudes are often augmented over a lesion. Consequently, for each frame, a new value is calculated in which the amplitude of the COG is multiplied by the inverse of the velocity. The resulting product (AMP/VEL) grows bigger for large, slow moving maxima (i.e., those characteristic of lesion-associated activity) and smaller for low, fast moving maxima. These calculations are graphically displayed along with trajectory plots (FIGS. 10-13) where they assist in the localization of pathology. Minima, maxima, and mean values form features as for the previously described calculations. Cumulative counts are also kept of the number of such maxima at each pixel.

FIGS. 10-13 show four BEAM images within a schematic outline of the head in vertex view, nose above, left ear to the left, and right ear to the right. Each image represents output of the STA procedure for a subject with untreated right lateral frontal lobe brain tumor. Each figure shows a trajectory plot, which comprises a string of dots, each representing the center of gravity (COG) of the region above the 25% maximum value of successive frames.

FIGS. 10-12 describe the trajectories in the interval 270-564 msec. The negative trajectory began posteriorly, traveled in the left hemisphere just to the left of the midline in an anterior direction and then swept into the left lateral frontal area. The sequence of the trajectory can be determined in real time as it is calculated.

In each figure certain COG are highlighted by larger white squares. The occurence of a white square indicates that at that point in the trajectory the amplitude, the inverse velocity, or the product thereof was in the top 12.5% of the magnitude range of the parameter being measured. In FIG. 10 the amplitude of the COG is measured (AMP). In FIG. 11 the inverse velocity of the COG is measured ($VEL^{-1}$). In FIG. 12 the measured value is the product of the amplitude and the inverse velocity (AMP/VEL), a measure that is of greatest magnitude for COG that are both slow and large (the condition which brain activity typically exhibits overlying a tumor). Note that in FIG. 10, amplitude barely delineates the lesion; in FIG. 11 inverse velocity shows the lesion, but in FIG. 12 the lesion is completely localized by the amplitude times inverse velocity function. FIG. 13 provides a reading of the entire 512 msec epoch. Note how the AMP/VEL measure shown over the entire AER accurately and distinctly locates the lesion.

We have found that the presence of high AMP/VEL points off of the midline is strongly indicative of pathology.

Further one should note the manner in which right lateral frontal tumor not only distorts peak trajectory in the overlying scalp, but also distorts trajectories in the corresponding region of the contralateral hemisphere. For example, in FIGS. 10-12 the negative trajectory is distorted into the left lateral frontal region.

FIG. 14 shows a distribution plot of negative COG (image G at left) and positive COG (image H at right). These plots can be directly used as templates or can be compared to control group subjects to form Z-SPM and templates. They are useful for generating features.

Another useful feature than can be derived from STA is the balance point (or center of gravity) of the trajectory itself. This gives the physician a single number that is correlated to the presence of pathology.

My copending application entitled "Cross Correlation Analysis in Brain Electrical Activity Mapping", filed on Apr. 13, 1987, is incorporated by reference.

Other embodiments of the invention are within the following claims.

What is claimed is:

1. The method of detecting and characterizing brain pathology in a patient, comprising the steps of:
    determining the patient's evoked potential data;
    preparing a brain electrical activity map representing said evoked potential data;
    determining the location of one or more peaks of said evoked potential data in each of a sequence of frames;
    calculating the center of gravity of said peaks for each frame;
    plotting said center of gravities in a single frame to provide a spatial trajectory of said evoked potential data; and
    detecting and characterizing brain pathology in the patient by comparing the appearance of said spatial trajectory to a comparable trajectory for normal patients.

2. The method of claim 1 wherein said step of plotting comprises plotting said center of gravities to provide a plurality of spatial trajectories in said single frame.

3. The method of claim 2 wherein said plurality of spatial trajectories includes separate negative and positive trajectories.

4. The method of claim 1 wherein said peaks are regions of a frame above a preselected percentage of the maximum value in that frame.

5. The method of claim 4 wherein each of said center of gravities is determined by computing the center of gravity of the perimeter of each of said regions.

6. The method of claim 5 wherein each of said center of gravities is computed by first computing the center of gravity of each segment of said perimeter and then computing the center of gravity of the segments.

7. The method of claim 1 wherein said peaks are only plotted in said trajectory if they come from a frame in which the maximum value exceeds a noise percentage defined as a percentage of the maximum value in all frames of the evoked potential data.

8. The method of claim 7 wherein said noise percentage is in the range from 10 to 25%.

9. The method of claim 1 wherein the presence of assymetrical trajectories is indicative of pathology.

10. The method of claim 1 wherein the balance point of a trajectory is determined to provide a single numerical feature.

11. The method of claim 1 wherein there is computed for each frame the product of the amplitude of the center of gravity and the inverse of the velocity of the center of gravity and wherein values of said product above a predetermined threshold are highlighted on said spatial trajectory.

12. The method of claim 1 wherein a numerical feature representative of one or more frames of the evoked potential is displayed on a display of the spatial trajectory by highlighting or otherwise changing the representation of a point along the trajectory that corresponds to that frame.

13. The method of claim 12 wherein said numerical feature is displayed as an enlarged point on the trajectory.

14. The method of claim 1 wherein said peak locations include negative and positive peaks.

* * * * *